United States Patent (10) Patent No.: US 11,205,306 B2
Soryal et al. (45) Date of Patent: Dec. 21, 2021

(54) AUGMENTED REALITY MEDICAL DIAGNOSTIC PROJECTION

(71) Applicant: AT&T Intellectual Property I, L.P., Atlanta, GA (US)

(72) Inventors: Joseph Soryal, Ridgewood, NY (US); Naila Jaoude, Eatontown, NJ (US); Samuel N. Zellner, Dunwoody, GA (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 0 days.

(21) Appl. No.: 16/418,248

(22) Filed: May 21, 2019

(65) Prior Publication Data

US 2020/0372714 A1 Nov. 26, 2020

(51) Int. Cl.
*A61B 90/00* (2016.01)
*G16H 10/60* (2018.01)
*G16H 50/20* (2018.01)
*G06T 19/00* (2011.01)
*G16H 30/20* (2018.01)
*G16H 15/00* (2018.01)
*G06F 3/01* (2006.01)
*G02B 27/01* (2006.01)

(52) U.S. Cl.
CPC ............ *G06T 19/006* (2013.01); *A61B 90/36* (2016.02); *G16H 10/60* (2018.01); *G16H 15/00* (2018.01); *G16H 30/20* (2018.01); *G16H 50/20* (2018.01); *A61B 2090/365* (2016.02); *A61B 2090/367* (2016.02); *A61B 2090/376* (2016.02); *G02B 2027/0138* (2013.01); *G06F 3/017* (2013.01); *G06T 2210/41* (2013.01)

(58) Field of Classification Search
CPC ....... G06T 19/006; G16H 10/60; G16H 50/20
See application file for complete search history.

(56) References Cited

U.S. PATENT DOCUMENTS

| | | | | |
|---|---|---|---|---|
| 2013/0268203 | A1* | 10/2013 | Pyloth | G16H 50/20 702/19 |
| 2014/0100874 | A1* | 4/2014 | Wood | G06F 19/00 705/3 |
| 2014/0267662 | A1* | 9/2014 | Lampo | G16H 20/40 348/77 |
| 2018/0256258 | A1* | 9/2018 | Nash | A61B 34/25 |
| 2019/0108915 | A1* | 4/2019 | Spurlock, III | G16H 50/70 |
| 2019/0302460 | A1* | 10/2019 | Kaul | G02B 27/017 |
| 2019/0333276 | A1* | 10/2019 | Brown | A61B 90/36 |
| 2020/0293174 | A1* | 9/2020 | Diaz | G06F 3/0485 |

* cited by examiner

Primary Examiner — Ryan McCulley

(57) ABSTRACT

Methods, computer-readable media, and apparatuses for presenting medical records associated with a body part of person via an augmented reality device are described. For example, a processing system including at least one processor may identify at least one body part of a person in a visual data feed of an augmented reality device, obtain based on the identifying at least a first medical record of the person that is associated with the at least one body part, obtain at least a second medical record of at least one relative of the person that is associated with the at least one body part, and present, via the augmented reality device, at least the first medical record and the least the second medical record.

20 Claims, 4 Drawing Sheets

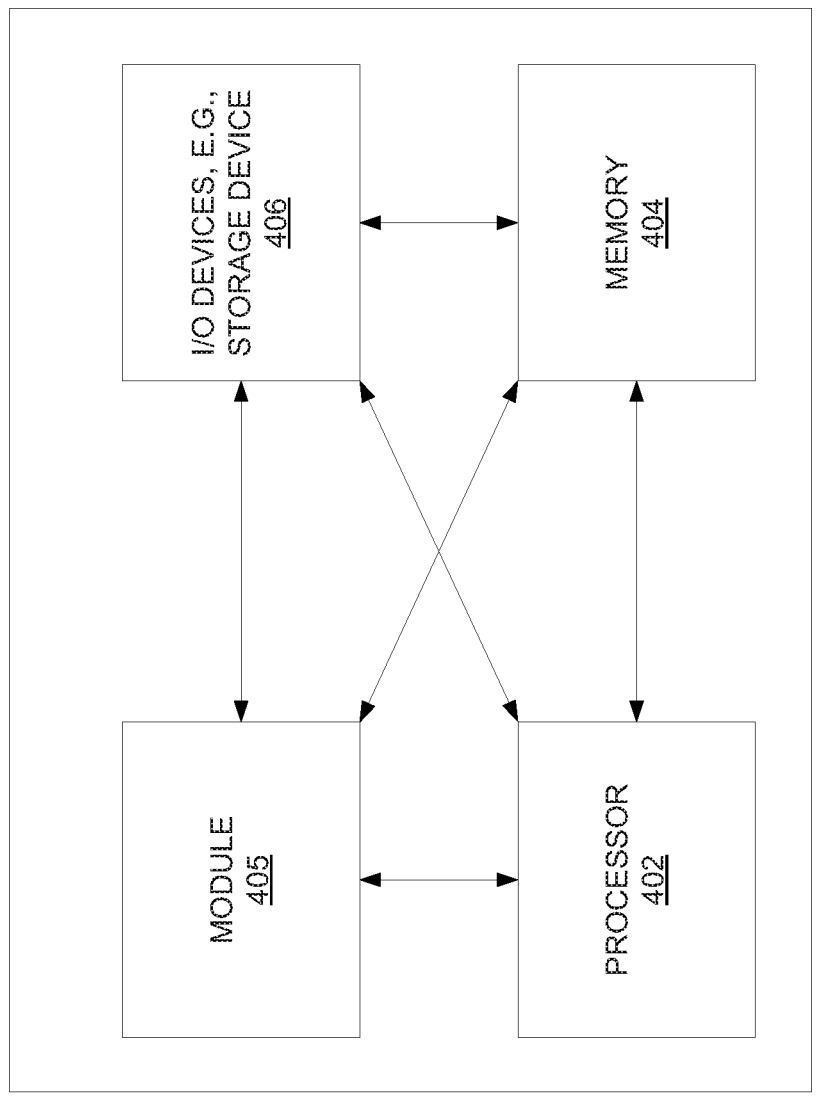

AUGMENTED REALITY MEDICAL DIAGNOSTIC PROJECTION

The present disclosure relates generally to augmented reality systems, and more particularly to methods, computer-readable media, and apparatuses for presenting medical records associated with a body part of a person via an augmented reality device.

SUMMARY

Methods, computer-readable media, and apparatuses for presenting medical records associated with a body part of a person via an augmented reality device are described. For example, a processing system including at least one processor may identify at least one body part of a person in a visual data feed of an augmented reality device, obtain based on the identifying at least a first medical record of the person that is associated with the at least one body part, obtain at least a second medical record of at least one relative of the person that is associated with the at least one body part, and present, via the augmented reality device, at least the first medical record and at least the second medical record.

BRIEF DESCRIPTION OF THE DRAWINGS

The teachings of the present disclosure can be readily understood by considering the following detailed description in conjunction with the accompanying drawings, in which:

FIG. 4 illustrates a high level block diagram of a computing device specifically programmed to perform the steps, functions, blocks and/or operations described herein.

To facilitate understanding, identical reference numerals have been used, where possible, to designate identical elements that are common to the figures.

DETAILED DESCRIPTION

Figure 1:
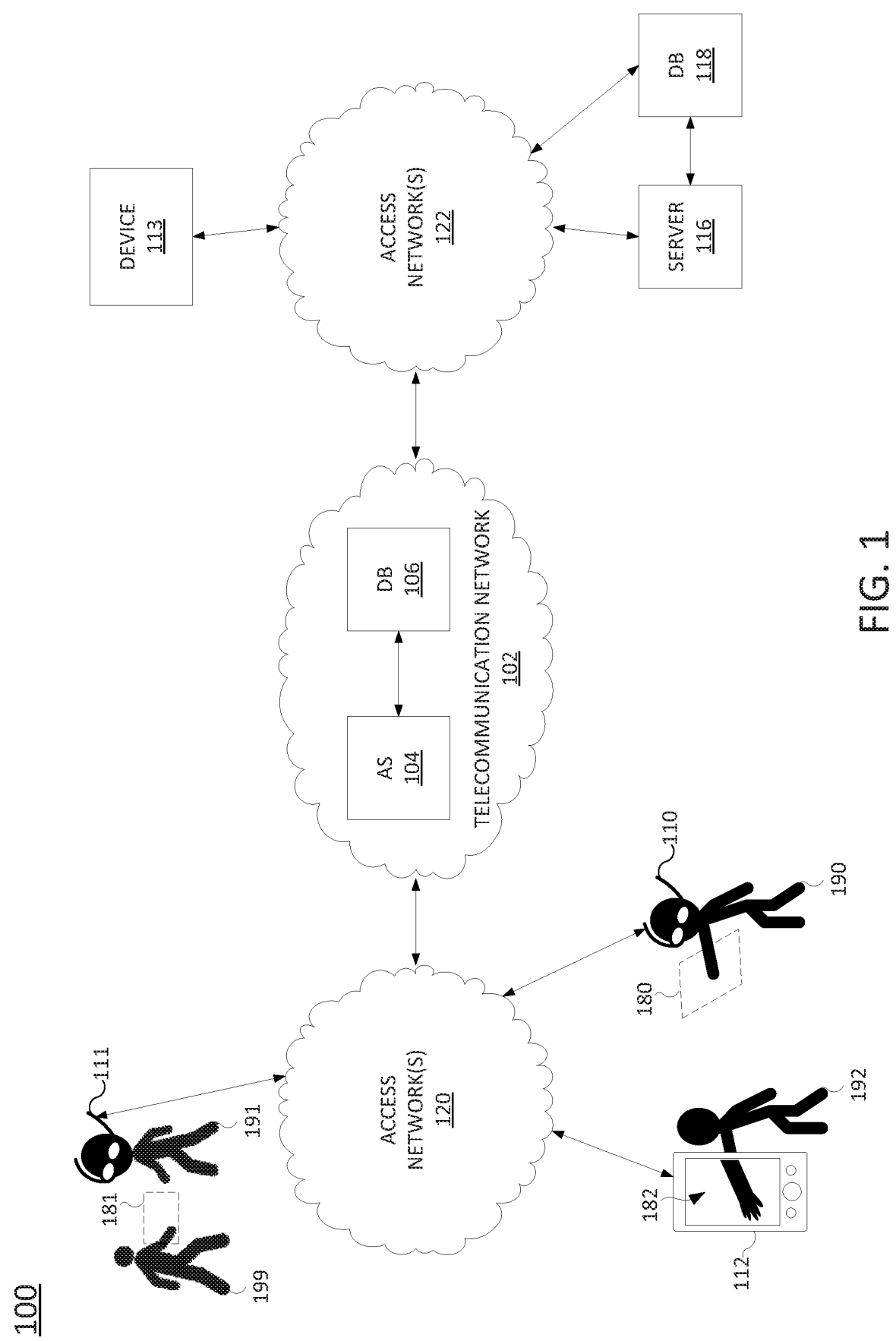
FIG. 1 illustrates an example network related to the present disclosure.

Examples of the present disclosure include superimposing a user's (e.g., a patient's) own medical history and family medical history over imaging of an augmented reality device, in addition to information regarding similar cases of other patients with the same circumstances to help diagnose and treat various medical conditions. In one example, the present disclosure provides an interactive model via augmented reality (AR) between a patient and a healthcare provider. In one example, systems of the present disclosure may provide diagnostic predictions, and may also search for and recommend medical providers based on the diagnostic predictions.

In one example, a patient's historical medical records are digitized and form layers that are superimposed on the current imaging of an augmented reality (AR) device. Each event (e.g., a bone fracture, an infection, a prior surgical procedure performed on a body part of interest, a cancer tissue, etc.) may comprise a layer, where layers are historical and/or related to events. In one example, a last layer may include a diagnostic prediction that is determined via a machine learning module that compares other patients' results and progressions of one or more medical conditions. For instance, in one example, a system of the present disclosure may correlate a present visual feed (e.g., visual data relating to a certain part of the body captured in images and/or video from an AR device) with an event. To illustrate, a doctor may be looking at a patient's arm with an AR device (e.g., an AR headset/glasses). The system may then superimpose layers into the doctor's field of view via the AR device containing medical records related to the arm. This may include relevant information related to the arm (e.g., medical histories of the patient and of the patient's relatives (broadly any person who is connected with another or others by blood or marriage, e.g., parents, siblings, uncles, aunts, grandparents, cousins, nieces, nephews and so on), images, potential diagnoses, drugs, treatments, and so forth). In one example, the AR device may recognize various body parts of a human, and may perform the correlation and obtain other matching information from the patient's history, the history of the patient's family, as well as from epidemiologic data (e.g., anonymized statistical data from various patients in a geographic area, or other demographic grouping), anonymized case studies, or indirectly related events (e.g., knowledge of possible exposure to a certain bacteria due to a recent visit to a particular healthcare facility, knowledge of recent travel to a particular region, etc.). In another example, the AR device may forward a visual feed to a network-based processing system to perform the same or similar functions, and the results may be provided by the processing system to the AR device for presentation.

In either case, systems of the present disclosure may identify organs/body parts via the AR device through the following mechanisms: shapes of body parts for different ages, genders, etc., and also with anomalies in shapes as a result of disease, birth defect, and/or genetics, the location of each organ in the body, relative position(s) to other body parts, and the connectivity to other organs, the flow of fluids in/out of an organ, e.g., heart, lungs, liver, kidney, etc., the periodic movements of an organ (e.g., heart beats, inhalation/exhalation, etc.) In one example, a healthcare provider or a self-examining person may also bias the system to identify a part of the body.

In one example, the AR device may respond to voice commands or other user inputs to zoom in with respect to certain areas of the body and to bring/remove layers from the overlay on the field of view. In one example, systems of the present disclosure may also be used by non-medical professionals for self-examination and self-diagnosis. For instance, a user may view a portion of his/her body via an AR device. Then, the AR device and/or other network-based components of the system may provide medical history information and diagnostic predictions, and may also recommend to connect with certain medical professionals, e.g., specialists associated with one or more of the diagnostic predictions. In one example, the AR device and/or other system component(s) may automatically connect with a device of medical professional to provide the medical professional with the same visual feed as well as the additional information, e.g., user/patient medical history, family medical history, diagnostic prediction(s), etc. In one example, the medical professional may be granted remote control via his or her device to select/deselect layers, to change the focus of the area on the body, to bias the system for certain suspected conditions, and so forth. This allows the medical professional to remotely view the body part of interest overlaid with the relevant medical information.

In one example, the system may also provide recommended drug treatments, recommended therapy procedures, recommended surgical procedures, or other recommended interventions based upon one or more diagnostic predictions. For instance, the system may store or have access to one or more databases which store correlations between diagnostic predictions and possible courses of treatment. In one example, systems of the present disclosure may include one or more machine learning (ML) models which may use pattern recognition to find similar cases to the condition or diagnostic prediction from one or more data repositories. For example, the ML models may use any classification and pattern recognition set of algorithms, such as classification supervised algorithms and clustering unsupervised algorithms, to predict categorical labels, and multilinear subspace learning algorithms to predict labels of multi-dimensional data.

To illustrate, information from a visual feed from the AR device, user/patient history, family history, and possible user input from the user/patient and/or medical professional may comprise inputs to the ML model(s), which may output potential diagnosis and treatment plans. In one example, the system may use a profile for a user/patient with current conditions, past conditions, family history, and/or medical professional input. The system may then search through one or more data repositories for similar profiles with the highest matching scores. For instance, more similar situations correspond to higher matching scores and vice versa. In addition, similar cases may have more weight in the decision making process for determining a diagnostic predictions. For example, if there is a 40 year old male subject and the data repository contains a first event record for a 38 year old male subject with all the conditions matched and a second event record for 28 year old male sample patient with all the conditions matched, the diagnosis from the event related to the 38 year old may have more impact or relevance in the decision by the ML model than the 28 years old's case. Aside from age, other parameters may indicate additional relevance between the subjects, e.g., similar family medical history, similar ethic background, similar diet (e.g., smokers versus non-smokers), similar related environmental working conditions (e.g., working in a coal mine, working in a factory, working in an office building, working on a ship, working on night shifts, etc.) and so on. These and other aspects of the present disclosure are described in greater detail below in connection with the examples of FIGS. 1-4.

To further aid in understanding the present disclosure, FIG. 1 illustrates an example system 100 in which examples of the present disclosure for presenting medical records associated with a body part of a person via an augmented reality device may operate. The system 100 may include any one or more types of communication networks, such as a traditional circuit switched network (e.g., a public switched telephone network (PSTN)) or a packet network such as an Internet Protocol (IP) network (e.g., an IP Multimedia Subsystem (IMS) network), an asynchronous transfer mode (ATM) network, a wireless network, a cellular network (e.g., 2G, 3G, 4G, 5G and the like), a long term evolution (LTE) network, and the like, related to the current disclosure. It should be noted that an IP network is broadly defined as a network that uses Internet Protocol to exchange data packets. Additional example IP networks include Voice over IP (VoIP) networks, Service over IP (SoIP) networks, and the like.

In one example, the system 100 may comprise a telecommunication network 102. The telecommunication network 102 may be in communication with one or more access networks 120 and 122, and the Internet (not shown). In one example, telecommunication network 102 may combine core network components of a cellular network with components of a triple play service network; where triple-play services include telephone services, Internet services and television services to subscribers. For example, telecommunication network 102 may functionally comprise a fixed mobile convergence (FMC) network, e.g., an IP Multimedia Subsystem (IMS) network. In addition, telecommunication network 102 may functionally comprise a telephony network, e.g., an Internet Protocol/Multi-Protocol Label Switching (IP/MPLS) backbone network utilizing Session Initiation Protocol (SIP) for circuit-switched and Voice over Internet Protocol (VoIP) telephony services. Telecommunication network 102 may further comprise a broadcast television network, e.g., a traditional cable provider network or an Internet Protocol Television (IPTV) network, as well as an Internet Service Provider (ISP) network. In one example, telecommunication network 102 may include a plurality of television (TV) servers (e.g., a broadcast server, a cable head-end), a plurality of content servers, an advertising server (AS), an interactive TV/video on demand (VoD) server, and so forth. For ease of illustration, various additional elements of network 102 are omitted from FIG. 1.

In one example, the access networks 120 and 122 may comprise Digital Subscriber Line (DSL) networks, public switched telephone network (PSTN) access networks, broadband cable access networks, Local Area Networks (LANs), wireless access networks (e.g., an Institute for Electrical and Electronics Engineers (IEEE) 802.11/Wi-Fi network and the like), cellular access networks, $3^{rd}$ party networks, and the like. For example, the operator of telecommunication network 102 may provide a cable television service, an IPTV service, or any other types of telecommunication service to subscribers via access networks 120 and 122. In one example, the access networks 120 and 122 may comprise different types of access networks, may comprise the same type of access network, or some access networks may be the same type of access network and other may be different types of access networks. In one embodiment, the telecommunication network 102 may be operated by a telecommunication network service provider. The telecommunication network 102 and the access networks 120 and 122 may be operated by different service providers, the same service provider or a combination thereof, or may be operated by entities having core businesses that are not related to telecommunications services, e.g., corporate, governmental or educational institution LANs, and the like.

In one example, the access networks 120 may be in communication with one or more devices 110-112. Similarly, access networks 122 may be in communication with one or more devices, e.g., device 113, server 116, database (DB 118), and so forth. Access networks 120 and 122 may transmit and receive communications between devices 110-113, between devices 110-113, and server 116 and/or database (DB) 118, application server 104 and/or database (DB) 106, other components of telecommunication network 102, devices reachable via the internet in general, and so forth. In one example, each of the devices 110-113 may comprise any single device or combination of devices that may comprise a user endpoint device. For example, the devices 110-113 may each comprise a mobile device, a cellular smart phone, a laptop, a tablet computer, a desktop computer, an application server, a bank or cluster of such devices, and the like. In one example, devices 110-112 may comprise AR devices such as heads-up displays, wearable or non-wearable optical see-through or video see-through devices, handheld computing devices with at least a camera and a display, and so forth. For instance, as illustrated in FIG. 1, devices 110 and 111 may comprise wearable computing devices (e.g., smart glasses, augmented reality glasses, headsets, or the like). Similarly, device 112 may comprise a tablet computer, cellular smartphone and/or non-cellular wireless device, or the like with at least a camera and a display.

In one example, devices 110-113 may each comprise programs, logic or instructions for performing functions in connection with examples of the present disclosure for presenting medical records associated with a body part of a person via an augmented reality device. For example, devices 110-113 may each comprise a computing system or device, such as computing system 400 depicted in FIG. 4, and may be configured to provide one or more operations or functions in connection with examples of the present disclosure for presenting medical records associated with a body part of a person via an augmented reality device, as described herein.

In one example, the access networks 122 may also be in communication with a server 116 and a database (DB) 118. The server 116 and DB 118 may be associated with a service, or system for presenting medical records associated with a body part of a person via an augmented reality device, as described herein. In accordance with the present disclosure, server 116 may comprise a computing system or server, such as computing system 400 depicted in FIG. 4, and may be configured to provide one or more operations or functions for presenting medical records associated with a body part of a person via an augmented reality device, as described herein. It should be noted that as used herein, the terms "configure," and "reconfigure" may refer to programming or loading a processing system with computer-readable/computer-executable instructions, code, and/or programs, e.g., in a distributed or non-distributed memory, which when executed by a processor, or processors, of the processing system within a same device or within distributed devices, may cause the processing system to perform various functions. Such terms may also encompass providing variables, data values, tables, objects, or other data structures or the like which may cause a processing system executing computer-readable instructions, code, and/or programs to function differently depending upon the values of the variables or other data structures that are provided. As referred to herein a "processing system" may comprise a computing device including one or more processors, or cores (e.g., as illustrated in FIG. 4 and discussed below) or multiple computing devices collectively configured to perform various steps, functions, and/or operations in accordance with the present disclosure.

In one example, DB 118 may comprise a physical storage device integrated with server 116 (e.g., a database server), or attached or coupled to the server 116, to store various types of information in support of systems for presenting medical records associated with a body part of a person via an augmented reality device, in accordance with the present disclosure. For example, DB 118 may store individual medical records, may store indications of relations among individuals (e.g., to obtain medical records of relatives of a person), may store information regarding patterns for detecting body parts, for detecting particular motions associated with body parts, for detecting conditions of body parts, etc., may store machine learning-based modules (e.g., ML models) for making diagnostic predictions based upon body part conditions of subject persons, medical records of the persons, medical records of relatives, and/or user inputs, may store information for automatically contacting medical providers or other caregivers on behalf of a person, and so forth that may be processed by server 116 or provided to devices requesting medical records and/or any other information outlined above from server 116.

To illustrate, server 116 may identify at least one body part of a person in a visual data feed of an AR device, obtain at least a first medical record of the person that is associated with the at least one body part, obtain at least a second medical record of at least one relative of the person that is associated with the at least one body part, and present, via the augmented reality device, at least the first medical record and at least the second medical record. For example, the presenting may include projecting a transparent overlay of at least the first medical record and at least the second medical record via the AR device.

In one example, the AR device may comprise one of the devices 110-112, and the body part may be of one of the persons 190, 199, or 192, respectively. In one example, a user, e.g., person 190 or 192 may be examining himself or herself directly with his or her own device 110 or 112. For instance, the respective fields of view 180 and 182 may include the hands of users 190 and 192, respectively. In another example, the AR device may be used by a doctor or other caregivers, or simply a second person viewing a first person with the AR device, e.g., person 191 viewing person 199 via device 111. For instance, the field of view 181 via device 111 may include a hand of the person 199. In this regard, the presenting may include providing the medical records and instructions by server 116 to the AR device to cause the medical records to be projected by the AR device via a transparent overlay, e.g., in one of field of views 180-182. For instance, devices 110 and 111 may present the medical information via projector(s) and reflector(s) or the like, while device 112 may present the medical information via a display screen that is also presenting the information from the visual feed, e.g., the hand and arm of user 192.

In one example, the server 116 may identify the at least one body part via a machine learning-based pattern detection in accordance with information from a visual data feed from the augmented reality device (e.g., one of the devices 110-112). In one example, the server 116 may detect a motion associated with the at least one body part, e.g., a cough, a heartbeat pattern, a vascular/blood flow pattern, a movement pattern of a mouth during speech, a tremor in the at least one body part (e.g., one or more body parts), and so forth. In one example, the server 116 may determine at least one condition associated with the at least one body part based upon the visual data feed, such as detecting a mole on the skin, a mole pattern, a sunburn or sunburn pattern, a skin infection, a lesion, a swollen joint, swollen skin, etc., or detecting arrhythmia, detecting facial paralysis and/or facial droop, and so on.

In one example, the server 116 may select at least the first medical record from among a plurality of medical records of the person (e.g., person 190, 192, or 199) and the second medical record from among a plurality of medical records of relatives of the subject person based upon the at least one body part, such as a hand, and/or a condition of the at least one body part, in addition to a user input. For example, the user input may include a suspected condition of the person, a preference for a type of medical record, or a preference for medical records associated with the at least one body part. The user input may come from the subject person (e.g., person 190, 192, and/or 199 via devices 111-112, respectively), or may come from another user (e.g., a medical professional, caregiver, or the like, such as person 191 via device 111 or another person via device 113). To illustrate, a doctor, e.g., person 191, may suspect that a patient, e.g., person 199, may have a fractured wrist and may provide a user input to focus upon the wrist, medical records associated with the wrist, hands, forearm, or related body parts, and so forth. The user input may comprise verbal commands or natural language speech which may be captured via device 111 and forwarded to server 116, for example. However, in other, further, and different examples, the user input may be of a different form, such as text input via a keyboard, selection from among a plurality of options via a mouse in connection with a graphical user interface, hand gestures captured via a camera of the device 111, and so forth. Accordingly, server 116 may focus upon identifying the at least one body part in accordance with the user input. For instance, there may be multiple body parts in field of view 181 among which the server 116 may select one or more for initial consideration. Alternatively, or in addition, server 116 may select medical records which are related to the at least one body part or region of the body of interest, and/or related to a suspected condition of the person in accordance with the user input.

In one example, server 116 may generate at least a first diagnostic prediction based upon the at least one condition of the at least one body part in the visual data feed. The at least the first diagnostic prediction may further be based upon: at least the first medical record, at least the second medical record, and/or the user input. In one example, the server 116 may generate the first diagnostic prediction via a machine learning-based pattern detection in accordance with the at least one condition of the at least one body part. For instance, server 116 may utilize one or more patterns or "signatures" stored in DB 118 that may be used to identify different diagnostic predictions. The patterns/signatures may include various data points, or factors, including visual information from the visual feeds, information from the person's medical records, and the medical records of relatives.

To illustrate, the visual information may include at least one condition associated with the at least one body part that is detected from the visual data feed, such as a facial droop. The data points may also include medical records of the subject person and/or his or her relative(s) which may indicate a history of stroke in the subject individual or in his/her family members, or a recent history of viral infection. The server 116 may then match the at least one condition of the at least one body part in the visual data feed, at least the first medical record, and at least the second medical record to one or more possible diagnostic predictions. For instance, the subject person may have Bell's palsy from viral infection or other causes, or may have had a stroke. If the subject person's medical records reveal recent viral infection, or additional data (anonymized over many individuals) from the geographic area indicate that treatment for viral infection is prevalent in the area, the server 116 may be more likely to determine a diagnostic prediction of Bell's palsy. On the other hand, if family medical records reveal that parents, siblings, or other relatives have a history of stroke, the server 116 may be more likely to determine a diagnostic prediction of stroke.

In addition, in one example, one or more user inputs may impact pattern matching/recognition by differentially weighting different factors depending upon the particular user input(s). For instance, a doctor's input regarding a suspected condition may bias the server 116 to be more likely to find a certain pattern match associated with a diagnostic prediction. For instance, the subject person and/or a medical professional may have greater reason to consider that the facial paralysis or facial droop may be stroke-related if there is awareness of a personal or family history of stroke that may be inaccessible to the server 116. Thus, a user input may bias the server 116 towards one diagnostic prediction or another.

The at least one diagnostic prediction may then be presented via the augmented reality device (e.g., device 111). For instance, the at least one diagnostic prediction may be projected in a transparent manner in the visual field of user 191, e.g., overlaid over field of view 181, along with at least the first medical record and at least the second medical record.

It should be noted that the medical records may also be selected based upon the user input. As such, there may be confirmation bias in terms of the input data selected. However, the present examples may be used as a tool to assist a doctor or other medical professionals in obtaining relevant medical records and achieving a diagnostic prediction. As such, the present disclosure is not intended to fully automate or replace customary interactions between medical professionals and patients in their care.

In one example, server 116 may accept additional user inputs to select additional medical records, to focus on one or more different body parts or additional body parts that may be identified within a field of view, and/or medical records relating thereto, and so forth. In one example, server 116 may accept additional user inputs to rule out or exclude suspected conditions to dismiss one or more diagnostic predictions, and so forth. In such examples, server 116 may then obtain additional medical records, present the additional medical records via the AR device (e.g., device 111), provide one or more additional diagnostic predictions, and so on. In other words, the server 116 may prioritize which medical record(s) to initially present in response to detecting a body part and/or movement related thereto. The server 116 can then receive one or more user inputs to call up additional medical records if a user is not satisfied with the initially presented medical records or would simply like to explore more medical records that may be related to the at least one body part, if the user would like to obtain additional diagnostic predictions beyond that/those initially provided, and so forth.

In one example, server 116 may present via the AR device, e.g., one of devices 110 or 112, a recommendation to establish a visual communication session between the AR device and a device of a medical professional (e.g., device 113) based upon at least the first diagnostic prediction. In one example, the visual communication session may be established via the AR device (e.g., device 110 or device 112) and the device of the medical professional (e.g., device 113), in response to an input from the person 190 or 192. Alternatively, the visual communication session may be automatically established based upon at least the first diagnostic prediction, e.g., when at least the first diagnostic prediction includes a suspected urgent medical condition. These and other aspects of the present disclosure are discussed in greater detail below in connection with the examples of FIGS. 2 and 3.

Although only a single server 116 and a single DB 118 are illustrated, it should be noted that any number of servers 116 or databases 118 may be deployed. In addition, server 116, DB 118, DB 106, server 104, and so forth may comprise public or private cloud computing resources, e.g., one or more host devices/servers in one or more data centers to host virtual machines (VMs), containers, or the like comprising various functions, services, and so on.

In one example, telecommunication network 102 may also include an application server 104 and a database 106. In one example, AS 104 may perform the same or similar functions as server 116. Similarly, DB 106 may store the same or similar information as DB 118, e.g., medical records, indications of relations among individuals, information regarding patterns for detecting body parts, particular motions associated with body parts, conditions of body parts, etc., machine learning-based modules for making diagnostic predictions based upon body part conditions of subject persons, medical records of the persons, medical records of relatives, and/or user inputs, information for automatically contacting medical providers or other caregivers on behalf of a person, and so forth, programs, logic, or instructions that may be executed by AS 104 or server 116 for presenting medical records associated with a body part of a person via an augmented reality device in accordance with the present disclosure, and so forth. For instance, telecommunication network 102 may provide a service for presenting medical records associated with a body part of a person via an augmented reality device to subscribers, e.g., in addition to television, phone, and/or other telecommunication services. In one example, AS 104, DB 106, server 116, and/or DB 118 may operate in a distributed and/or coordinated manner to perform various steps, functions, and/or operations described herein. In one example, application server 104 may comprise network function virtualization infrastructure (NFVI), e.g., one or more devices or servers that are available as host devices to host virtual machines (VMs), containers, or the like comprising virtual network functions (VNFs). In other words, at least a portion of the network 102 may incorporate software-defined network (SDN) components.

It should be noted that the system 100 has been simplified. Thus, the system 100 may be implemented in a different form than that which is illustrated in FIG. 1, or may be expanded by including additional endpoint devices, access networks, network elements, application servers, etc. without altering the scope of the present disclosure. In addition, system 100 may be altered to omit various elements, substitute elements for devices that perform the same or similar functions, combine elements that are illustrated as separate devices, and/or implement network elements as functions that are spread across several devices that operate collectively as the respective network elements. For example, the system 100 may include other network elements (not shown) such as border elements, routers, switches, policy servers, security devices, gateways, a content distribution network (CDN) and the like. For example, portions of telecommunication network 102 and/or access networks 120 and 122 may comprise a content distribution network (CDN) having ingest servers, edge servers, and the like.

Similarly, although only two access networks 120 and 122 are shown, in other examples, access networks 120 and/or 122 may each comprise a plurality of different access networks that may interface with telecommunication network 102 independently or in a chained manner. For example, device 113 and server 116 may access telecommunication network 102 via different access networks, devices 110-112 may access telecommunication network 102 via different access networks, and so forth. Thus, these and other modifications are all contemplated within the scope of the present disclosure.

Figure 2:
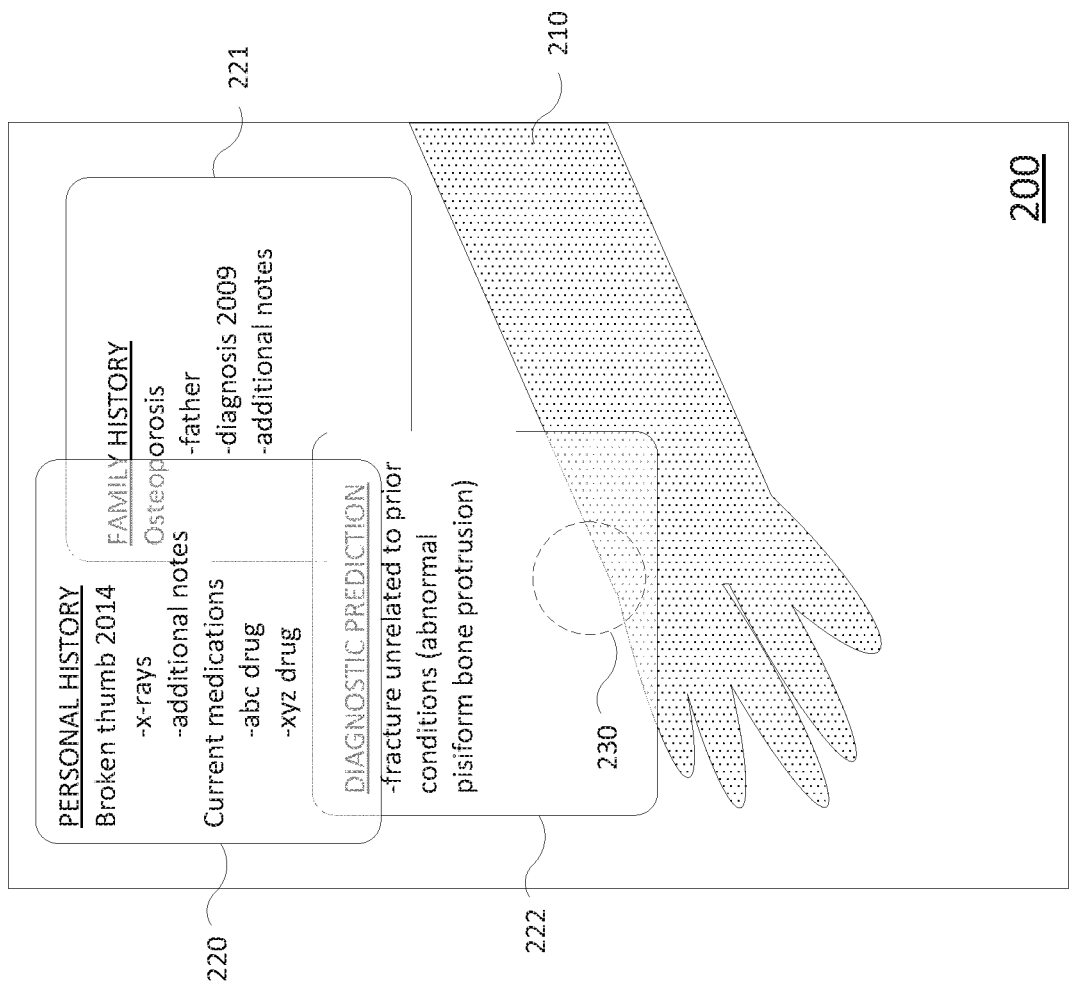
FIG. 2 illustrates an example process in accordance with the present disclosure.

FIG. 2 illustrates an example AR field of view in accordance with examples of the present disclosure for presenting medical records associated with a body part of a person via an augmented reality device. As illustrated in FIG. 2, the field of view 200 includes an image of a portion 210 of a person's body (e.g., including a forearm, hand, and wrist). As described above, the field of view 200 may be that of a user via an AR device. For instance, the field of view 200 may be that of the subject person examining the portion 210 of his or her own body, or may be that of a medical provider examining the subject person. As also described above, the AR device and/or other components of network-based processing system may identify at least one body part in a visual data feed. For instance a camera of the AR device may capture the portion 210 of the body in the field of view 200, and the AR device and/or other components of a network-based processing system may identify the presence of a forearm, wrist, hand, etc. via pattern recognition, e.g., in accordance with one or more machine learning modules. In addition, the AR device and/or other components of a network-based processing system may obtain medical records of the subject person and one or more relatives of the subject person (e.g., the medical records associated with at least one body part that is identified).

The medical records may then be presented via the AR device. For instance, the medical records may be presented in one or more layers, or tiles, e.g., as transparent visual overlays in/on the field of view 200. For example, medical records of the subject person may be presented in a first tile, or layer 220, and medical records of the subject person's family may be presented in a second tile, or layer 221. In the present example, the AR device and/or other components of a network-based processing system may access medical records which indicate that the subject person had a broken thumb in a prior year, e.g., the year 2014. Although not specifically related to the portion 210 of the body of the subject person in the field of view 200, the medical records may also indicate that the subject person is currently taking the following medications: abc drug and xyz drug. This type of information may be deemed important enough that it should be presented regardless of the specific aspect of the body within the field of view 200.

Similarly, the AR device and/or other components of a network-based processing system may access family medical records which indicate that the subject person's father was diagnosed with osteoporosis in 2009, which may be presented in summary form in layer 221. In one example, aspects of the information in the layers 220 and 221 may include links which may provide additional information, for instance a user input via voice command or other modalities (such as a gesture that may be captured and recognized via a camera of the AR device) may select "x-rays" which may cause the actual x-ray images from the subject person's broken thumb to be displayed in the same layer or a new layer.

Additionally, the AR device and/or other components of a network-based processing system may generate a diagnostic prediction on the basis of the visual data feed from the field of view 200, the personal and family medical records, any additional user inputs, and so on. To illustrate, in the present example, the AR device and/or other components of a network-based processing system may identify a swollen pisiform bone protrusion of the wrist from the visual data feed of the field of view 200 (indicated by the region 230 in FIG. 2). Although the AR device and/or other components of a network-based processing system may be biased to make a diagnostic prediction related to the subject person's prior medical history or familial history (such as osteoporosis), in the present case the visual data indicates a swollen pisiform bone protrusion, which appears to be unrelated to these prior personal and familial medical conditions. As such, the AR device and/or other components of a network-based processing system may reach a diagnostic prediction of possible fracture unrelated to prior conditions. In addition, the diagnostic prediction may be presented in a third tile, or layer 222 in/on the field of view 200 to inform the subject person or medical professional utilizing the AR device.

It should be noted that the foregoing is just one example of the types of human parts (e.g., limps, organs, etc.), medical histories, and diagnostic predictions that may be determined and identified in accordance with the present disclosure. For instance, in another example, a field of view may include a face of a user, from which the AR device and/or other components of a network-based processing system may identify a face, may identify a condition of the face (e.g., facial droop), may obtain medical records indicating a personal and/or family history of stroke, may determine a diagnostic prediction of stroke based upon the visual information and/or medical histories, and so on. Thus, these and other examples are all contemplated within the scope of the present disclosure.

Figure 3:
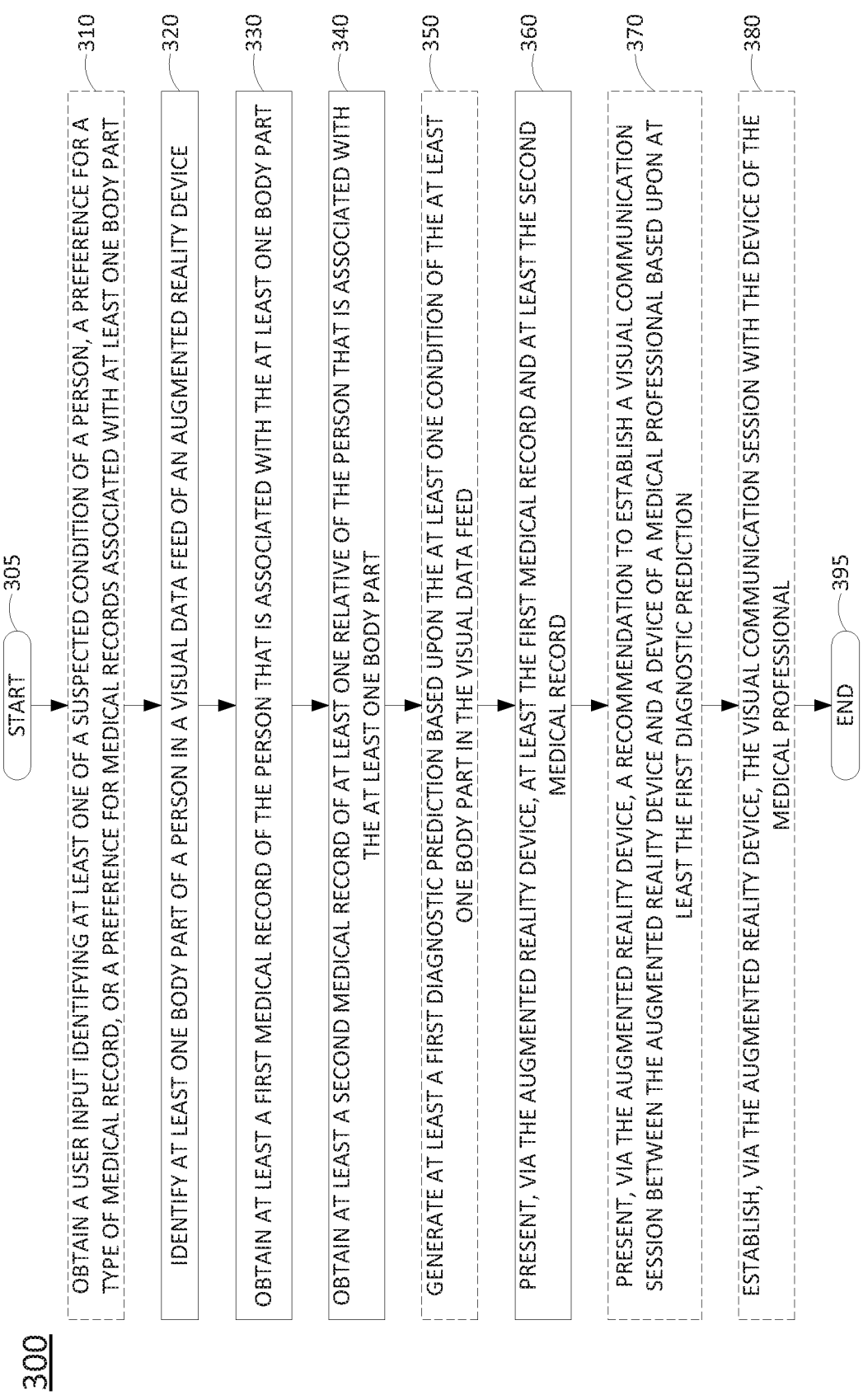
FIG. 3 illustrates a flowchart of an example method for presenting medical records associated with a body part of a person via an augmented reality device.

FIG. 3 illustrates a flowchart of an example method 300 for presenting medical records associated with a body part of a person via an augmented reality device, in accordance with the present disclosure. In one example, the method 300 is performed by a component of the system 100 of FIG. 1, such as by one of the server 116, application server 104, or any of the devices 110-112, and/or any one or more components thereof (e.g., a processor, or processors, performing operations stored in and loaded from a memory), or by one or more of the server 116, application server 104, or any one of the devices 110-112 in conjunction with one or more other devices, such as a different one or more of server 116, application server 104, or any one of the devices 110-112, and/or one or more of DB 106, DB 118, device 114, and so forth. In one example, the steps, functions, or operations of method 300 may be performed by a computing device or system 400, and/or processor 402 as described in connection with FIG. 4 below. For instance, the computing device or system 400 may represent any one or more components of a server 116, application server 104, and/or a device 110-112 in FIG. 1 that is/are configured to perform the steps, functions and/or operations of the method 300. Similarly, in one example, the steps, functions, or operations of method 300 may be performed by a processing system comprising one or more computing devices collectively configured to perform various steps, functions, and/or operations of the method 300. For instance, multiple instances of the computing device or processing system 400 may collectively function as a processing system. For illustrative purposes, the method 300 is described in greater detail below in connection with an example performed by a processing system. The method 300 begins in step 305 and proceeds to step 310.

At optional step 310, the processing system may obtain a user input identifying at least one of a suspected condition of a person, a preference for a type of medical record, or a preference for medical records associated with the at least one body part. The user input may originate from the subject person or may originate from another user (e.g., a medical professional, a caregiver, or the like). For instance, the subject person, a medical professional, or other caregiver may be examining the person via an AR device. In one example the AR device comprises the processing system. Alternatively, or in addition, the processing system may comprise a network-based processing system in communication with the AR device.

At step 320, the processing system identifies at least one body part of a person in a visual data feed of the AR device. The AR device may be used by the subject person or by a medical professional or other caregivers while examining the person. In one example, the visual data feed may be captured by an outward-facing camera of the AR device that is directed at the at least one body part. In one example, the identifying of the at least one body part comprises detecting a motion associated with the at least one body part. For instance, the motion may comprise a cough, a heartbeat pattern, a vascular/blood flow pattern, a movement pattern of a mouth during speech, a tremor in the at least one body part (e.g., one or more body parts), and so forth. In one example, the identifying the at least one body part is via a machine learning-based pattern detection in accordance with information from the visual data feed. In one example, the identifying the at least one body part comprises determining at least one condition associated with the at least one body part based upon the visual data feed. For instance, the processing system may detect a mole on the skin, a mole pattern, a sunburn or sunburn pattern, a skin infection, a lesion, a swollen joint, swollen skin, etc. Similarly, the processing system may detect a pulse arrhythmia, a facial paralysis and/or facial droop, and so forth. In one example, the identifying the at least one condition of the at least one body part is via a machine learning-based pattern detection in accordance with information from the visual data feed.

At step 330, the processing system obtains at least a first medical record of the person that is associated with the at least one body part. In one example, step 330 may include selecting at least the first medical record from among a plurality of medical records of the person based upon the at least one body part that is identified at step 320 and/or the user input that may be obtained at optional step 310. In one example, at least the first medical record may be selected further based upon a movement related to the at least one body part that may be detected at step 320 and/or at least one condition associated with the body part that may be detected at step 320. In other words, the processing system may prioritize which medical record(s) of the subject person to initially obtain (e.g., for presentation at step 360) in response to detecting the body part and/or a movement or condition related thereto.

At step 340, the processing system obtains at least a second medical record of at least one relative of the person that is associated with the at least one body part. In one example, step 340 may include selecting at least the second medical record from among a plurality of medical records of the at least one relative based upon the at least one body part that is identified at step 320 and the user input that may be obtained at optional step 310. In one example, at least the second medical record may be selected further based upon a movement related to the at least one body part that may be detected at step 320 and/or at least one condition associated with the body part that may be detected at step 320. In other words, the processing system may prioritize which medical record(s) of the at least one relative to initially obtain (e.g., for presentation at step 360) in response to detecting the body part and/or a movement or condition related thereto. It should be noted that any presentation of medical records of any individuals must be previously authorized by those individuals, e.g., parents of a child may preauthorize the release of their medical records in assisting the treatment of their child. However, in order to ensure that the individuals' confidential medical information is protected, positive and specific preauthorization must be received prior to the usage of such medical information from such individuals even though the patient is related to such individuals.

At optional step 350, the processing system may generate at least a first diagnostic prediction based upon the at least one condition of the at least one body part in the visual data feed. The at least the first diagnostic prediction may further be based upon one or both of at least the first medical record or at least the second medical record. In one example, the first diagnostic prediction is generated via a machine learning-based pattern detection in accordance with the at least one condition of the at least one body part in the visual data feed. For instance, the processing system may utilize one or more patterns or "signatures" stored in a database accessible to the processing system that may be used to identify different diagnostic predictions. The patterns/signatures may include various data points, or factors, relating to visual information from visual feeds, information from a subject person's medical records, and the medical records of relatives. In one example, at least the first diagnostic prediction may further be based on user (e.g., one or more medical professionals) input that may be obtained at optional step 310. For instance, if the information from the visual data feed is consistent with a suspected medical condition, the processing system may be more likely to generate at least the first diagnostic prediction that is consistent with the suspected medical condition. In other words, at least the first diagnostic prediction may comprise the suspected medical condition. However, where the visual data feed, at least the first medical record, and/or at least the second medical record are inconsistent with or would tend to indicate that the suspected medical condition is not present, the processing system may generate a different diagnostic prediction that is consistent with the available information of the visual data feed, at least the first medical record, and/or at least the second medical record.

To illustrate, the least one condition detected from the visual data feed may comprise a facial droop. The data points may also include medical records of the subject person and/or his or her relative(s) (who preauthorized such use) which may indicate a history of stroke in the subject individual or in his/her family members, or a recent history of viral infection. The processing system may then match the at least one condition of the at least one body part in the visual data feed, at least the first medical record, and at least the second medical record, to one or more possible diagnostic predictions. For instance, the subject person may have Bell's palsy from viral infection or other causes, or may have had a stroke. If the subject person's medical records reveal recent viral infection, or additional data (e.g., anonymized over many unknown individuals and/or preauthorized from such individuals) from a relevant geographic area (e.g., a city, a county, a state, etc.) indicate that treatment for viral infection is prevalent in the area, the processing system may be more likely to determine a diagnostic prediction of Bell's palsy. On the other hand, if family medical records reveal that parents, siblings, or other relatives have a history of stroke, the processing system may be more likely to determine a diagnostic prediction of stroke. In addition, in one example, one or more user inputs may impact pattern matching/recognition by differentially weighting different factors. For instance, a suspected condition may bias the processing system to be more likely to find a certain pattern match associated with a diagnostic prediction.

At step 360, the processing system presents, via the AR device, at least the first medical record and at least the second medical record. In one example, step 360 further comprises presenting at least the first diagnostic prediction of optional step 350 via the AR device. In one example, step 360 may comprise projecting a transparent overlay of at least the first medical record and at least the second medical record via the AR device. For instance, an example of transparent overlay via an AR device is illustrated in FIG. 2.

At optional step 370, the processing system may present, via the AR device, a recommendation to establish a visual communication session between the AR device and a device of a medical professional based upon at least the first diagnostic prediction of optional step 350 (e.g., in an example where the AR device is used by the person). For example, at least the first diagnostic prediction may relate to a suspected medical condition for which examination by a medical professional is deemed warranted. For instance, a database available to the processing system may store indications for which given diagnostic predictions should result in a recommendation for communication with a medical professional.

At optional step 380, the processing system may establish, via the AR device, the visual communication session with the device of the medical professional. In one example, the visual communication session may be established in response to an input from the person (e.g., having been presented with the recommendation at optional step 370). In another example, the visual communication session may be established based upon at least the first diagnostic prediction (e.g., automatically, without specific user input). For instance, the establishment of the visual communication session may be automatic when at least the first diagnostic prediction includes a suspected urgent medical condition. For instance, a database available to the processing system may store indications for which given diagnostic predictions should result in automatic communication with a medical professional.

Following step 350 or any one or more of optional steps 360-380 the method 300 proceeds to step 395 where the method ends.

It should be noted that the method 300 may be expanded to include additional steps, or may be modified to replace steps with different steps, to combine steps, to omit steps, to perform steps in a different order, and so forth. For instance, in one example the processing system may repeat one or more steps of the method 300, such as steps 320-360, steps 310-380, etc. For example, a user may direct a camera of the AR device toward one or more additional or different body parts, which may result in obtaining different medical records, different diagnostic predictions, and so forth. In another example, the method 300 may be expanded to include receive one or more additional user inputs to call up additional medical records, to dismiss one or more of the at least one diagnostic prediction, to provide one or more additional suspected medical conditions, and so forth. For instance, the AR device and/or the processing system may accept and respond to user inputs if a user is not satisfied with the initially presented medical records, if the user would like to explore more medical records that may be related to the at least one body part, if the user would like to examine the presented medical records in more detail, and so on. Thus, these and other modifications are all contemplated within the scope of the present disclosure.

In addition, although not expressly specified above, one or more steps of the method 300 may include a storing, displaying and/or outputting step as required for a particular application. In other words, any data, records, fields, and/or intermediate results discussed in the method can be stored, displayed and/or outputted to another device as required for a particular application. Furthermore, operations, steps, or blocks in FIG. 3 that recite a determining operation or involve a decision do not necessarily require that both branches of the determining operation be practiced. In other words, one of the branches of the determining operation can be deemed as an optional step. However, the use of the term "optional step" is intended to only reflect different variations of a particular illustrative embodiment and is not intended to indicate that steps not labelled as optional steps to be deemed to be essential steps. Furthermore, operations, steps or blocks of the above described method(s) can be combined, separated, and/or performed in a different order from that described above, without departing from the example embodiments of the present disclosure.

FIG. 4 depicts a high-level block diagram of a computing device or processing system specifically programmed to perform the functions described herein. For example, any one or more components or devices illustrated in FIG. 1 or described in connection with the method 300 may be implemented as the processing system 400. As depicted in FIG. 4, the processing system 400 comprises one or more hardware processor elements 402 (e.g., a microprocessor, a central processing unit (CPU) and the like), a memory 404, (e.g., random access memory (RAM), read only memory (ROM), a disk drive, an optical drive, a magnetic drive, and/or a Universal Serial Bus (USB) drive), a module 405 for presenting medical records associated with a body part of a person via an augmented reality device, and various input/output devices 406, e.g., a camera, a video camera, storage devices, including but not limited to, a tape drive, a floppy drive, a hard disk drive or a compact disk drive, a receiver, a transmitter, a speaker, a display, a speech synthesizer, an output port, and a user input device (such as a keyboard, a keypad, a mouse, and the like).

Although only one processor element is shown, it should be noted that the computing device may employ a plurality of processor elements. Furthermore, although only one computing device is shown in the Figure, if the method(s) as discussed above is implemented in a distributed or parallel manner for a particular illustrative example, i.e., the steps of the above method(s) or the entire method(s) are implemented across multiple or parallel computing devices, e.g., a processing system, then the computing device of this Figure is intended to represent each of those multiple computers. Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented. The hardware processor 402 can also be configured or programmed to cause other devices to perform one or more operations as discussed above. In other words, the hardware processor 402 may serve the function of a central controller directing other devices to perform the one or more operations as discussed above.

It should be noted that the present disclosure can be implemented in software and/or in a combination of software and hardware, e.g., using application specific integrated circuits (ASIC), a programmable logic array (PLA), including a field-programmable gate array (FPGA), or a state machine deployed on a hardware device, a computing device, or any other hardware equivalents, e.g., computer readable instructions pertaining to the method(s) discussed above can be used to configure a hardware processor to perform the steps, functions and/or operations of the above disclosed method(s). In one example, instructions and data for the present module or process 405 for presenting medical records associated with a body part of a person via an augmented reality device (e.g., a software program comprising computer-executable instructions) can be loaded into memory 404 and executed by hardware processor element 402 to implement the steps, functions or operations as discussed above in connection with the example method 300. Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method(s) can be perceived as a programmed processor or a specialized processor. As such, the present module 405 for presenting medical records associated with a body part of a person via an augmented reality device (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. Furthermore, a "tangible" computer-readable storage device or medium comprises a physical device, a hardware device, or a device that is discernible by the touch. More specifically, the computer-readable storage device may comprise any physical devices that provide the ability to store information such as data and/or instructions to be accessed by a processor or a computing device such as a computer or an application server.

While various embodiments have been described above, it should be understood that they have been presented by way of example only, and not limitation. Thus, the breadth and scope of a preferred embodiment should not be limited by any of the above-described example embodiments, but should be defined only in accordance with the following claims and their equivalents.

What is claimed is:

1. A method comprising:
obtaining, by a processing system including at least one processor, a user input identifying at least one of:
a suspected condition of a person; or
a preference for medical records associated with at least one body part;
identifying, by the processing system, the at least one body part of the person in a visual data feed of an augmented reality device, wherein the identifying the at least one body part comprises determining at least one condition associated with the at least one body part based upon the visual data feed;
obtaining based on the identifying, by the processing system, at least a first medical record of the person that is associated with the at least one body part;
obtaining, by the processing system, at least a second medical record of at least one relative of the person that is associated with the at least one body part, wherein the obtaining the at least the second medical record comprises selecting the at least the second medical record from among a plurality of medical records of the at least one relative based upon the at least one body part that is identified, wherein the obtaining the at least the second medical record further comprises selecting the at least the second medical record from among the plurality of medical records of the at least one relative based upon the user input;
generating, by the processing system, at least a first diagnostic prediction via a first machine learning-based pattern detection based upon the at least one condition of the at least one body part in the visual data feed, the at least the first medical record, and the at least the second medical record; and presenting, by the processing system via the augmented reality device, the at least the first medical record, the at least the second medical record, and the at least the first diagnostic prediction, wherein the presenting comprises projecting a transparent overlay of the at least the first medical record, the at least the second medical record, and the at least the first diagnostic prediction via the augmented reality device.

2. The method of claim 1, where the identifying the at least one body part comprises detecting a motion associated with the at least one body part.

3. The method of claim 1, wherein the obtaining the at least the first medical record comprises selecting the at least the first medical record from among a plurality of medical records of the person based upon the at least one body part that is identified and the user input.

4. The method of claim 1, wherein the identifying the at least one body part is via at least a second machine learning-based pattern detection in accordance with information from the visual data feed.

5. The method of claim 4, wherein the identifying the at least one condition of the at least one body part is via the at least the second machine learning-based pattern detection in accordance with the information from the visual data feed.

6. The method of claim 1, further comprising:
presenting, via the augmented reality device, a recommendation to establish a visual communication session between the augmented reality device and a device of a medical professional based upon the at least the first diagnostic prediction, wherein the augmented reality device is used by the person.

7. The method of claim 6, further comprising:
establishing, via the augmented reality device, the visual communication session with the device of the medical professional, in response to an input from the person.

8. The method of claim 1, further comprising:
establishing, via the augmented reality device, a visual communication session with a device of a medical professional, based upon the at least the first diagnostic prediction.

9. The method of claim 1, wherein the augmented reality device comprises the processing system.

10. The method of claim 1, wherein the processing system is a network-based processing system in communication with the augmented reality device.

11. A non-transitory computer-readable medium storing instructions which, when executed by a processing system including at least one processor, cause the processing system to perform operations, the operations comprising:
obtaining a user input identifying at least one of:
a suspected condition of a person; or
a preference for medical records associated with at least one body part;
identifying the at least one body part of the person in a visual data feed of an augmented reality device, wherein the identifying the at least one body part comprises determining at least one condition associated with the at least one body part based upon the visual data feed;
obtaining based on the identifying at least a first medical record of the person that is associated with the at least one body part;
obtaining at least a second medical record of at least one relative of the person that is associated with the at least one body part, wherein the obtaining the at least the second medical record comprises selecting the at least the second medical record from among a plurality of medical records of the at least one relative based upon the at least one body part that is identified, wherein the obtaining the at least the second medical record further comprises selecting the at least the second medical record from among the plurality of medical records of the at least one relative based upon the user input;
generating at least a first diagnostic prediction via a first machine learning-based pattern detection based upon the at least one condition of the at least one body part in the visual data feed, the at least the first medical record, and the at least the second medical record; and
presenting, via the augmented reality device, the at least the first medical record, the at least the second medical record, and the at least the first diagnostic prediction, wherein the presenting comprises projecting a transparent overlay of the at least the first medical record, the at least the second medical record, and the at least the first diagnostic prediction via the augmented reality device.

12. An apparatus comprising:
a processing system including at least one processor; and
a computer-readable medium storing instructions which, when executed by the processing system, cause the processing system to perform operations, the operations comprising:
obtaining a user input identifying at least one of:
a suspected condition of a person; or
a preference for medical records associated with at least one body part;
identifying the at least one body part of the person in a visual data feed of an augmented reality device, wherein the identifying the at least one body part comprises determining at least one condition associated with the at least one body part based upon the visual data feed;
obtaining based on the identifying at least a first medical record of the person that is associated with the at least one body part;
obtaining at least a second medical record of at least one relative of the person that is associated with the at least one body part, wherein the obtaining the at least the second medical record comprises selecting the at least the second medical record from among a plurality of medical records of the at least one relative based upon the at least one body part that is identified, wherein the obtaining the at least the second medical record further comprises selecting the at least the second medical record from among the plurality of medical records of the at least one relative based upon the user input;
generating at least a first diagnostic prediction via a first machine learning-based pattern detection based upon the at least one condition of the at least one body part in the visual data feed, the at least the first medical record, and the at least the second medical record; and
presenting, via the augmented reality device, the at least the first medical record, the at least the second medical record, and the at least the first diagnostic prediction, wherein the presenting comprises projecting a transparent overlay of the at least the first medical record, the at least the second medical record, and the at least the first diagnostic prediction via the augmented reality device.

13. The apparatus of claim 12, where the identifying the at least one body part comprises detecting a motion associated with the at least one body part.

14. The apparatus of claim 12, wherein the obtaining the at least the first medical record comprises selecting the at least the first medical record from among a plurality of medical records of the person based upon the at least one body part that is identified and the user input.

15. The apparatus of claim 12, wherein the identifying the at least one body part is via at least a second machine learning-based pattern detection in accordance with information from the visual data feed.

16. The apparatus of claim 15, wherein the identifying the at least one condition of the at least one body part is via the at least the second machine learning-based pattern detection in accordance with the information from the visual data feed.

17. The apparatus of claim 12, the operations further comprising:
presenting, via the augmented reality device, a recommendation to establish a visual communication session between the augmented reality device and a device of a medical professional based upon the at least the first diagnostic prediction, wherein the augmented reality device is used by the person.

18. The apparatus of claim 17, the operations further comprising:
establishing, via the augmented reality device, the visual communication session with the device of the medical professional, in response to an input from the person.

19. The apparatus of claim 12, the operations further comprising:
establishing, via the augmented reality device, a visual communication session with a device of a medical professional, based upon the at least the first diagnostic prediction.

20. The apparatus of claim 12, wherein the augmented reality device comprises the processing system.

* * * * *